US006762328B2

United States Patent
Saayman et al.

(10) Patent No.: US 6,762,328 B2
(45) Date of Patent: *Jul. 13, 2004

(54) PROCESS FOR PRODUCTION OF MIBK USING CD TECHNOLOGY

(75) Inventors: Nelis Saayman, Vanderbljlpark (ZA); Grand James Lund, Randburg (ZA); Sybrandus Kindermans, Sasolburg (ZA)

(73) Assignee: Catalytic Distillation Technologies, Pasadena, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 10/289,693

(22) Filed: Nov. 7, 2002

(65) Prior Publication Data

US 2003/0065227 A1 Apr. 3, 2003

Related U.S. Application Data

(63) Continuation of application No. 09/951,295, filed on Sep. 11, 2001, now Pat. No. 6,518,462.

(30) Foreign Application Priority Data

| Sep. 15, 2000 | (ZA) | .......................................... | 2000/4929 |
| Sep. 3, 2001 | (ZA) | .......................................... | 2001/7297 |

(51) Int. Cl.[7] .............................................. C07C 45/00
(52) U.S. Cl. ...................... 568/392; 568/396; 568/401; 568/402
(58) Field of Search ................................ 568/392, 396, 568/401, 402

(56) References Cited

U.S. PATENT DOCUMENTS

| 3,666,816 A | 5/1972 | Takagi et al. ................ 260/593 |
| 3,953,517 A | 4/1976 | Schmitt et al. ......... 260/593 R |
| 4,306,068 A | 12/1981 | Smith, Jr. .................... 546/184 |
| 4,332,968 A | 6/1982 | Smith, Jr. .................... 564/278 |
| 5,059,724 A | 10/1991 | Chen et al. .................. 568/396 |
| 5,149,881 A | 9/1992 | Ushikubo et al. ........... 568/396 |
| 5,684,207 A | 11/1997 | Chen et al. .................. 568/396 |
| 6,008,416 A | 12/1999 | Lawson et al. ............. 568/396 |
| 6,518,462 B2 * | 2/2003 | Saayman et al. ........... 568/392 |

* cited by examiner

*Primary Examiner*—Johann Richter
*Assistant Examiner*—Sikarl A. Witherspoon
(74) *Attorney, Agent, or Firm*—Kenneth H. Johnson

(57) ABSTRACT

A process for producing methyl isobutyl ketone includes introducing acetone into a catalytic distillation. Some of the acetone is converted to mesityl oxide ('MSO'), water and, optionally, diacetone alcohol ('DAA') and/or other by-products. A product stream comprising MSO, water, and, optionally, DAA, other by-products and/or unreacted acetone is withdrawn from the catalytic distillation zone. When the product stream includes DAA, other by-products and/or unreacted acetone, it is treated in a treatment zone to remove at least some of the DAA, other by-products and/or the unreacted acetone therefrom. The product stream and hydrogen are fed into a reaction zone in which MSO present in the product stream and hydrogen react to form methyl isobutyl ketone ('MIBK'). A MIBK rich product stream is withdrawn from this reaction zone. Both a markup and clean copy of the substitute Abstract are attached to this amendment.

14 Claims, 3 Drawing Sheets

PROCESS FOR PRODUCTION OF MIBK USING CD TECHNOLOGY

This is a continuation, of application Ser. No. 09/951.295, filed Sep. 11, 2001, Now U.S. Pat. No. 6,518,462.

BACKGROUND OF THE INVENTION

FIELD OF THE INVENTION

This invention relates to the production of methyl isobutyl ketone. It relates in particular to a process for the production of methyl isobutyl ketone.

SUMMARY OF THE INVENTION

According to a first aspect of the invention, there is provided a process for producing methyl isobutyl ketone, which process includes introducing acetone as a feedstock into a first reaction zone;

subjecting the acetone to catalytic distillation in the first reaction zone, thereby to convert at least some of the acetone to mesityl oxide ('MSO'), water and, optionally, diacetone alcohol ('DAA') and/or other by-products;

withdrawing from the first reaction zone, a product stream comprising MSO, water, and, optionally, DAA, other by-products and/or unreacted acetone;

when the product stream includes DAA, other by-products and/or unreacted acetone, treating the product stream in at least one treatment zone to remove at least some of the DAA, other by-products and/or the unreacted acetone therefrom;

feeding the product stream, as well as hydrogen, into a second reaction zone in which MSO present in the product stream and hydrogen react to form methyl isobutyl ketone ('MIBK'); and withdrawing a MIBK rich product stream from the second reaction zone.

DETAILED DESCRIPTION AND PREFERRED EMBODIMENTS

Figure 1:
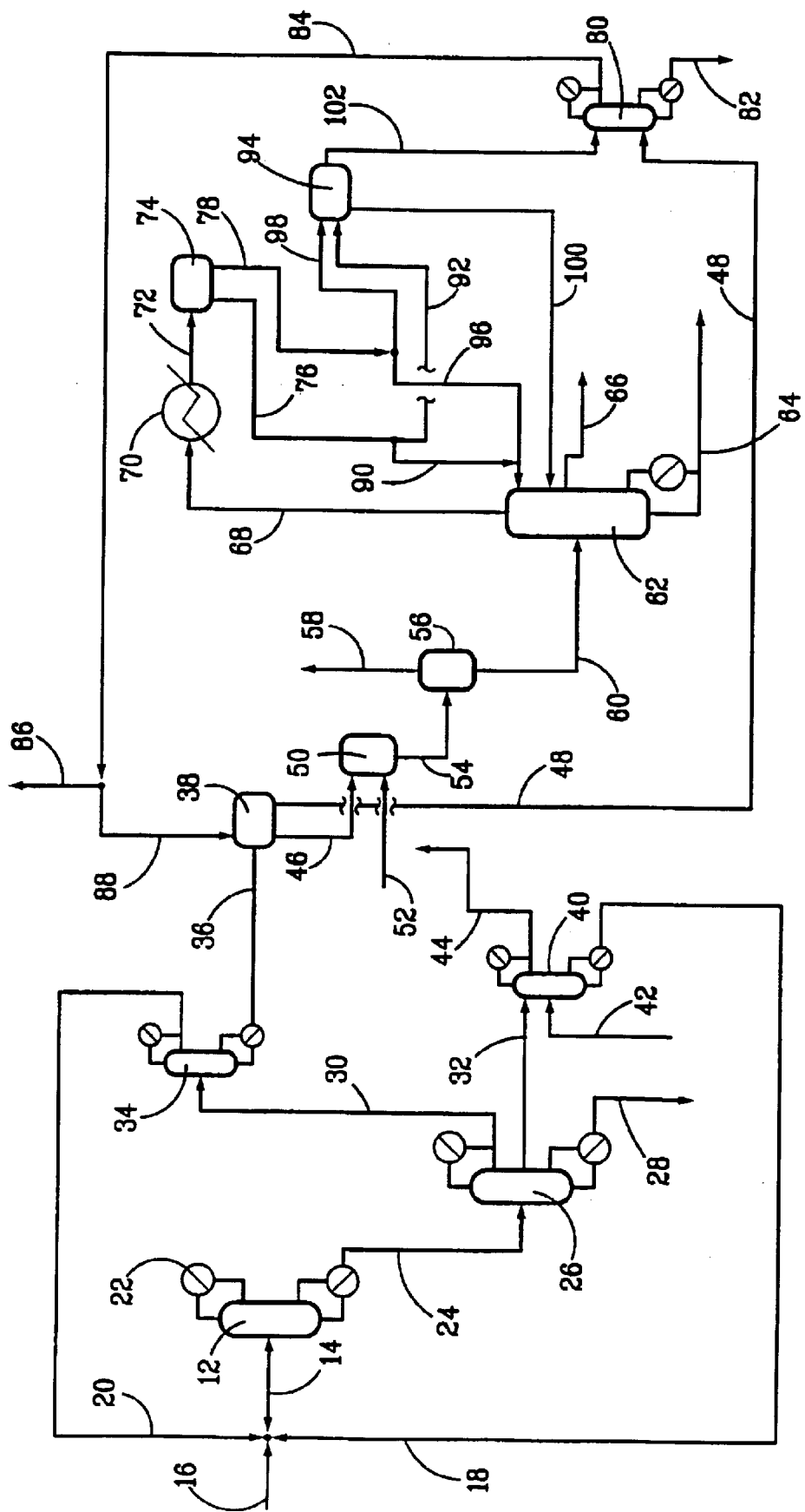
FIG. 1 shows a simplified flow diagram of a process according to a first embodiment of the invention for producing methyl isobutyl ketone.

The catalytic distillation in the first reaction zone involves effecting chemical reactions, under the influence of a catalyst, simultaneously with, or in combination with, distillation in a single zone. The catalyst used may be an acidic catalyst. More particularly, the catalyst may be an ion exchange resin such as a divinyl benzene based cation exchange resin, a styrene based cation exchange resin, an Amberlyst (trademark) resin such as Amberlyst 15, or the like; a zeolite; or alumina; however, a cation exchange resin is preferred. As resins have temperature limitations, the temperature conditions in the first reaction zone should not exceed the maximum catalyst operating temperature.

The first reaction zone will typically be provided by a column. The catalyst may be in particulate form, and may be arranged in the form of a packed bed located in the column. The acetone may enter the column at any point or level relative to the catalyst bed. Suitable distillation media, e.g. random packing, structured packing, trays or any other distillation apparatus or equipment, are then provided in the column below and/or above the catalyst bed, i.e. in at least one distillation zone of the column.

The temperature and pressure inside the column are such that the acetone is at its boiling point at the column pressure. In other words, the temperature inside the column is controlled by means of pressure. Preferably, temperature conditions in the column are from 50° C. to 300° C., more preferably from 100° C. to 135° C. in the catalyst bed.

The DAA, MSO, water, any other by-products that are formed and condensed unreacted acetone pass to the bottom of the column; these components may be reboiled in a reboiling stage or reboiler located at the bottom of the column. The DAA, MSO, water and any other by-products, which have higher boiling points than acetone and are thus not significantly vaporized by the reboiling, may be removed from the bottom of the column as the product stream, which can, however, also still contain some unreacted condensed acetone. However, instead, the reboiling stage may be operated at a sufficiently high temperature so that most of the DAA that is formed decomposes, thereby minimizing DAA production. The process may then include withdrawing a bottoms stream comprising heavy by-products such as trimethylbenzene ('TMB'), phorones, isophorones, non-decomposed DAA and MSO, as well as withdrawing, as a side stream, the product stream comprising mainly MSO and water. The side stream may then preferably be withdrawn between the bottom of the catalyst bed and the column bottom, to minimize the unreacted acetone and DAA that report to the side stream.

Any unreacted vaporized acetone may be withdrawn from the top of the column, condensed, and at least a portion thereof returned as a reflux to the column, at or above the catalyst bed. Any condensed unreacted acetone which is not used as reflux, can be withdrawn, and may be recycled as feedstock to the catalytic distillation column. However, the catalytic distillation column is preferably run under total reflux, i.e. all the unreacted vaporized acetone which is withdrawn from the top of the column is condensed and returned to the column as reflux. The catalytic distillation column, i.e. the first reaction zone, is characterized thereby that no hydrogen is fed into it, i.e. there is no MIBK formation in the first reaction stage.

More specifically, in one embodiment of the invention, the catalytic distillation column may be operated such that a significant proportion of the acetone introduced as the feedstock, e.g. up to about 25%–30% by mass thereof, remains unreacted, with DAA as well as trimethylbenzene ('TMB'), phorone, isophorone and other heavier by-products forming during the catalytic distillation, so that the product stream, which is withdrawn as a bottoms stream, comprises, in addition to the DAA, MSO, water and the by-products, also a significant proportion of unreacted acetone.

Thus, the catalytic distillation column may be operated at a temperature of 100° C.–120° C., typically about 120° C., in the reaction zone, i.e. in the catalyst bed; a temperature of 120° C. to 150° C., typically about 134° C., in the reboiler; a pressure of 2–7 bar(abs.), typically about 6.1 bar(abs.); and under total reflux.

The process may then include the treatment of the product stream in the at least one treatment zone, to remove at least some of, and preferably most of, the unreacted acetone, DAA, TMB, phorone, isophorone (and any other heavier by-products) and water present in the product stream. The process may thus include feeding the product stream from the catalytic distillation unit into a first treatment zone in the form of a first treatment distillation column from which a phorone rich bottoms stream, a DAA and TMB rich side stream, and the phorone- and TMB poor overheads product stream are withdrawn; and feeding the product stream from the first distillation column into a second treatment distillation column from which a MSO rich bottoms product stream and a MSO poor acetone rich overheads stream are withdrawn.

The acetone rich overheads stream from the second treatment distillation column may be returned to the catalytic distillation column, as a portion or component of the feedstock to the catalytic distillation column.

The DAA and TMB rich side stream from the first treatment distillation column may be subjected to extractive distillation with water in a third treatment distillation column. DAA that is not extracted with the water is withdrawn, together with any MSO and other compounds present in the side stream, from the third treatment distillation column, and returned to the catalytic distillation column as a component of the feedstock thereof. A TMB rich overheads stream is withdrawn from the third treatment distillation column.

The bottoms product stream from the second treatment distillation column, and which comprises mainly MSO and water, may be fed to a decanting stage where most of the water is decanted or separated from the MSO, with a MSO rich water lean product stream being withdrawn from the decanting stage. This MSO rich stream is then fed into the second reaction zone, together with the hydrogen.

The second reaction zone may be provided by a hydrogenation reactor, in which the MSO and hydrogen react in the presence of a hydrogenation catalyst, to form the MIBK. The hydrogenation reactor may employ a fixed catalyst bed, with the catalyst thus being in particulate form. The catalyst may be a hydrogenation catalyst consisting of, or containing, one or more metals from Group VIII and Group IB of the Periodic Table of Elements such as a Ni on Al catalyst, a Pd on Al catalyst, or a Pd on C catalyst. The hydrogenation reactor may be operated at a temperature of 80° C.–250° C., typically about 150° C., and at a pressure of 0 bar(abs.) to 50 bar(abs.), typically about 10 bar(abs.).

In the hydrogenation reactor, substantially all of the MSO is converted, primarily to MIBK but with some methyl isobutyl carbinol ('MIBC') also forming. The process may thus include treating the product stream from the hydrogenation reactor to remove any excess hydrogen, and the MIBC. This treatment may include removing the excess or unreacted hydrogen in a flash stage or drum, and subjecting the MIBK and MIBC containing product stream from the flash stage to distillation in a fourth distillation column, from which MIBK may be removed as a side stream. A overheads stream, comprising an azeotropic mixture of MIBK and water, is withdrawn from the fourth distillation column, for further treatment, as is a bottoms stream comprising any residual heavy by-products and the MIBC. MIBC and any by-products may be worked up further.

In another embodiment of the invention, more specifically, the catalytic distillation column may be operated so that substantially all of the acetone is converted, with DAA forming during the catalytic distillation, so that the product stream, which is withdrawn as a bottoms stream, comprises substantially only MSO, DAA and water, with at most traces of residual acetone and other by-products being present therein.

This may be achieved, for example, by increasing the loading in the column. The catalytic distillation unit may be operated at a temperature of 100° C.–120° C., typically about 120° C., in the reaction zone, i.e. in the catalyst bed; a temperature of 120° C.–150° C., typically about 134° C., in the reboiler; a pressure of 2 bar to 7 bar(abs.), typically about 6.1 bar(abs.); and under total reflux.

The bottoms product stream from the catalytic distillation column may be fed into a decanting or separation stage where water is separated or decanted from the MSO/DAA/water product stream which is then fed to the second reaction zone, together with the hydrogen. The second reaction zone may be a second catalytic distillation column containing a hydrogenation catalyst. The catalytic distillation column may contain a number of reaction stages, and may also contain a packed bed of the hydrogenation catalyst in particulate form. The catalyst may be a hydrogenation catalyst as hereinbefore described. The catalytic distillation column may be operated at a temperature of 80° C.–250° C., typically about 150° C., and at a pressure of 0 to 20 bar(abs.), typically about 2 bar(abs.).

In the second catalytic distillation column, apart from the formation of MIBK, heavy by-products such as TMB, phorones, isophorones, hexylene glycol, trimethyl cyclohexanone and dimethyl isobutyl ketone are formed. These are withdrawn, together with unreacted DAA, as a bottoms stream. Lighter by-products such as isopropanol, trimethylcyclohexane, and MIBC also form, and these are withdrawn from the second catalytic distillation column, together with unreacted acetone and any unreacted hydrogen, and the MIBK, as an overheads stream.

The process may include using a partial vapour liquid condenser in the second catalytic distillation column, so that a portion of the overheads stream is in vapour form and a portion in liquid form.

The overheads MIBK rich product stream may then be subjected to further treatment. The further treatment may comprise feeding the vapour portion of the product stream to a flash stage or drum where any unreacted hydrogen and other by-products are flashed off; the residual liquid from the flash stage is then recombined with the liquid portion of the product stream to form a combined product stream. This combined product stream may then be fed to a first distillation column from which a MIBK bottoms stream, and an overheads stream, comprising an azeotropic mixture of water and MIBK, are withdrawn. The overheads stream may be subjected to further treatment to recover the MIBK, which is returned to the first distillation column.

In yet another embodiment of the invention, more specifically, a bottoms stream comprising mainly heavy by-products, non-decomposed DAA, and MSO, and a side stream comprising mainly MSO and water, may be withdrawn from the catalytic distillation column.

The catalytic distillation column may then be operated at a temperature of 100° C.–120 ° C., typically at about 120° C. in the reaction zone, ie in the catalyst bed; a temperature of 120° C. to 300° C., typically about 240° C., in the reboiling stage; a pressure of 2 bar to 7 bar(abs.), typically about 6.1 bar(abs.); and under total reflux.

The side stream, ie the product stream, may then be fed into a decanting or separating stage where water is separated or decanted from the MSO/water product stream, with a decanted water phase and a MSO-rich organic phase being withdrawn from the decanting stage.

The decanted water phase from the decanting stage may be subjected to water recovery in a water recovery stage or unit, which may be a distillation column. A bottoms water fraction and an overheads MSO-containing fraction are then withdrawn from the water recovery unit. The overheads fraction may be combined with the MSO-rich organic phase from the decanting stage, and this mixed stream may then be fed to an acetone recovery stage or unit, which may also be a distillation column.

An acetone-rich overheads stream as well as a MSO-rich bottoms product stream may be withdrawn from the acetone recovery stage.

The product stream from the acetone recovery stage may then be fed to the second reaction zone, together with the hydrogen. The second reaction zone may be provided by a hydrogenation reactor as hereinbefore described. The product stream from the hydrogenation reactor may be treated or worked up, as hereinbefore described, ie by passing it through a flash stage and then through a MIBK purification unit which is typically a distillation column. By selecting, in the hydrogenation reactor, a hydrogenation catalyst which is selective towards MIBK formation while minimizing MIBC formation, such as a palladium on alumina catalyst, the overheads stream from the MIBK purification unit can comprise on-spec (>99.5 wt %) MIBK.

Instead, however, the second reaction zone may be provided by a catalytic distillation column containing a hydrogenation catalyst, as hereinbefore described.

The acetone-rich overheads stream from the acetone recovery stage may be subjected to cooling, to condense gaseous components therein, and then subjected to phase separation to obtain an aqueous phase and an organic phase. The aqueous phase may be recycled to the water recovery stage; part of the organic phase may be recycled to the acetone recovery stage as reflux, while part thereof may be recycled to the catalytic distillation unit as a component of the feed to the catalytic distillation unit.

The invention will now be described in more detail with reference to the accompanying drawings.

Referring to FIG. 1, reference numeral 10 generally indicates a process for producing methyl isobutyl ketone, according to a first embodiment of the invention.

The process 10 includes a catalytic distillation column 12 which has 34 theoretical stages packed with Amberlyst 15 (trademark) particulate acidic ion exchange resin as catalyst. The column 12 thus contains a catalyst bed. Typically, there are no separation or distillation stages above the catalyst bed, and 5 separation or distillation stages below the catalyst bed. A feed flow line 14 leads into the column 12, with a fresh acetone make-up line 16, a DAA recycle line 18 and a acetone recycle line 20 leading into the line 14. The feed point, i.e. the level at which the feed line 14 enters the column 12, can be at any desired level. The column 12 has a condenser arrangement 22, and operates under total reflux.

A bottoms product withdrawal line 24 leads from the bottom of the column 12 to a first distillation column 26. Isophorone bottoms withdrawal line 28 leads from the bottom of the column 26, while an overheads product withdrawal line 30 leads from the top of the column 26. A side stream withdrawal line 32 also leads from the column 26. The line 30 leads into a second distillation column 34. The line 20 is an overheads withdrawal line leading from the top of the distillation column 34, while a bottoms product withdrawal line 36 also leads from the distillation column 34, to a decanter or separator 38.

The side stream 32 leads to a third distillation column 40, with a water feed line 42 also leading into the distillation column 40. The line 18 leads from the bottom of the column 40, while a overheads withdrawal line 44 leads from the top of the column 40.

A product withdrawal line 46 leads from the decanter 38, as does a water withdrawal line 48.

The line 46 leads into a hydrogenation reactor 50, as does a hydrogen feed line 52. The hydrogenation reactor 50 contains a bed of a Pd on Al catalyst in particulate form. A product withdrawal line 54 leads from the bottom of the reactor 50 to a flash drum 56, with a light products withdrawal line 58 leading from the top of the flash drum 56. A product withdrawal line 60 leads from the bottom of the drum 56, into a fourth distillation column 62. A heavy by-product bottoms withdrawal line 64 leads from the distillation column 62, as does a MIBK side stream withdrawal line 66. An overheads withdrawal line 68 leads from the top of the column 62 to a condenser 70, with a flow line 72 leading from the condenser 70 to a decanter or separator 74. A liquid organic phase withdrawal line 76 leads from the separator 74, as does a water phase withdrawal line 78.

The line 48 leads to a fifth distillation column 80. A water withdrawal line 82 leads from the bottom of the column 80, while an overheads withdrawal line 84 leads from the top of the column 80. The line 84 splits into a purge line 86 and a recycle line 88 which leads back into the separator or decanter 38.

The line 76 splits into a line 90 which returns to the top of the column 62, and a line 92 which leads to a decanter or separator 94. Similarly, the line 78 splits into a line 96 which returns to the top of the column 62, as well as a line 98 which leads into the decanter or separator 94. A MIBK line 100 leads from the decanter 94 back to the distillation column 62. A line 102 leads from the decanter 94 to the column 80.

In use, acetone is fed, along the line 14, as a feedstock into the catalytic distillation unit 12. The catalytic distillation unit 12 is operated under total reflux. The temperature in the catalyst bed is about 120° C., while the temperature in the reboiler is about 134° C. The pressure in the column 12 is about 6.1 bar(abs.). In the catalytic distillation column 12, a mixture of unreacted acetone (26% by mass of the feedstock acetone), DAA, MSO, water, TMB and phorone is produced. The phorone is obtained from the reaction between MSO and acetone.

Unreacted vaporized acetone is withdrawn from the top of the column as an overheads stream, condensed, and returned, in full, to the column, so that the column operates under total reflux. No acetone will thus normally be withdrawn along the line 22.

A product stream comprising DAA, MSO, water, TMB and phorone is withdrawn along the line 24, and enters the distillation column 26. About 10% by mass of the DAA that is produced in the column 12 decomposes to acetone.

In the distillation column 26, any heavy by-products, including the phorones, are removed as a bottoms product, along the line 28. All the TMB is recovered, together with some DAA and by-products, as a side stream, which passes along the line 32 into the distillation column 40 in which the TMB undergoes extractive distillation with water which enters along the line 42. In the feedstream that enters the distillation column 40, the TMB and DAA are present in the form of medium boiling azeotropes. In the column 40, the water forms a ternary, lower boiling azeotrope with TMB and DAA at lower concentrations of DAA. Thus, the amount of DAA that is lost can be minimized by the extraction thereof with water, in the distillation column 40. DAA, by-products and any MSO present that are not extracted with water are removed along the flow line 18 and recycled back to the catalytic distillation column 12, as a component of the feedstock thereto. Isophorone and other by-products are ultimately removed in the first distillation column 26, via line 28.

The position of the side stream of the column 26, i.e. the take-off of the line 32, will depend on the amount of heavy by-products produced and the amount taken out will be limited by the TMB production. Some MSO and by-products are removed with the DAA along the line 32, since this reduces the duty requirements of the column 26.

TMB is withdrawn from the column 40 along the line 44, as an overheads product.

The remaining products, as well as unreacted acetone, are withdrawn as overheads from the column 26 along the line 30 and pass into the distillation unit 34. In the distillation column 34, acetone, and some water, is recovered as an overheads stream, and is returned, along the line 20, as a feedstock component to the catalytic distillation unit 12.

A product stream, comprising mainly MSO and water, is withdrawn as a bottoms product from the column 34 and fed, along the line 36, to the decanter or separator 38. A water rich fraction is withdrawn from the decanter 38 along the line 48, and fed to the distillation column 80, to recover the water. An MSO rich stream, containing about 3% by mass water, is withdrawn from the decanter 38 along the line 46, and passes into the hydrogenation reactor 50 in which the MSO and hydrogen, which enters along the line 52, react to form MIBK. In the reactor 50, about 99,9% of the MSO is converted, with a selectivity to MIBK of 97% and to MIBC of 3%. The reactor 50 typically operates at a temperature of about 150° C., and at a pressure of about 10 bar(abs.).

A product stream is withdrawn from the reactor 50 along the line 54 and passes to the flash drum 56, from which unreacted hydrogen is removed along the flow line 58. The MIBK containing product stream passes along the flow line 60 to the distillation column 62.

Any MIBC present in the product stream is separated out in the column 62, and is withdrawn from the column 62 along the flow line 64, while on-spec MIBK is removed along the flow line 66.

The operation of the distillation column 62 is believed to be important, in terms of duty requirements etc, since the separation of MIBK and MIBC is difficult, and MIBK losses must be minimized.

An overheads stream, consisting of an azeotropic mixture of water and MIBK, is withdrawn along the line 68, condensed in the condenser 70, and separated into an organic phase and an aqueous phase in the decanter or separator 74. Some of the organic phase and some of the water phase is sent back to the column 62 as reflux along the lines 76, 90 and 78, 96 respectively, while the remainder of the organic phase and the water phase passes to the decanter 94 along the flow lines 76, 92 and 78, 98 respectively. An organic phase from the decanter 94 is fed back to the distillation column 62 along the line 100, and enters the distillation column 60 above the main feed point entry.

A water rich phase from the decanter 94 is fed, along the flow line 102, into the distillation column 80, together with the aqueous phase from the decanter 38 which passes along the flow line 48. Pure water is removed from the distillation column 80, along the flow line 82, while an overheads mixture, comprising mainly MSO and water, is withdrawn from the distillation column 80 along the flow line 84. This stream is recycled back to the decanter or separator 38, to recover the MSO. A small purge (about 5% by mass) passes through the purge line 86 to prevent light products (acetone and isopropanol) building up.

Figure 2:
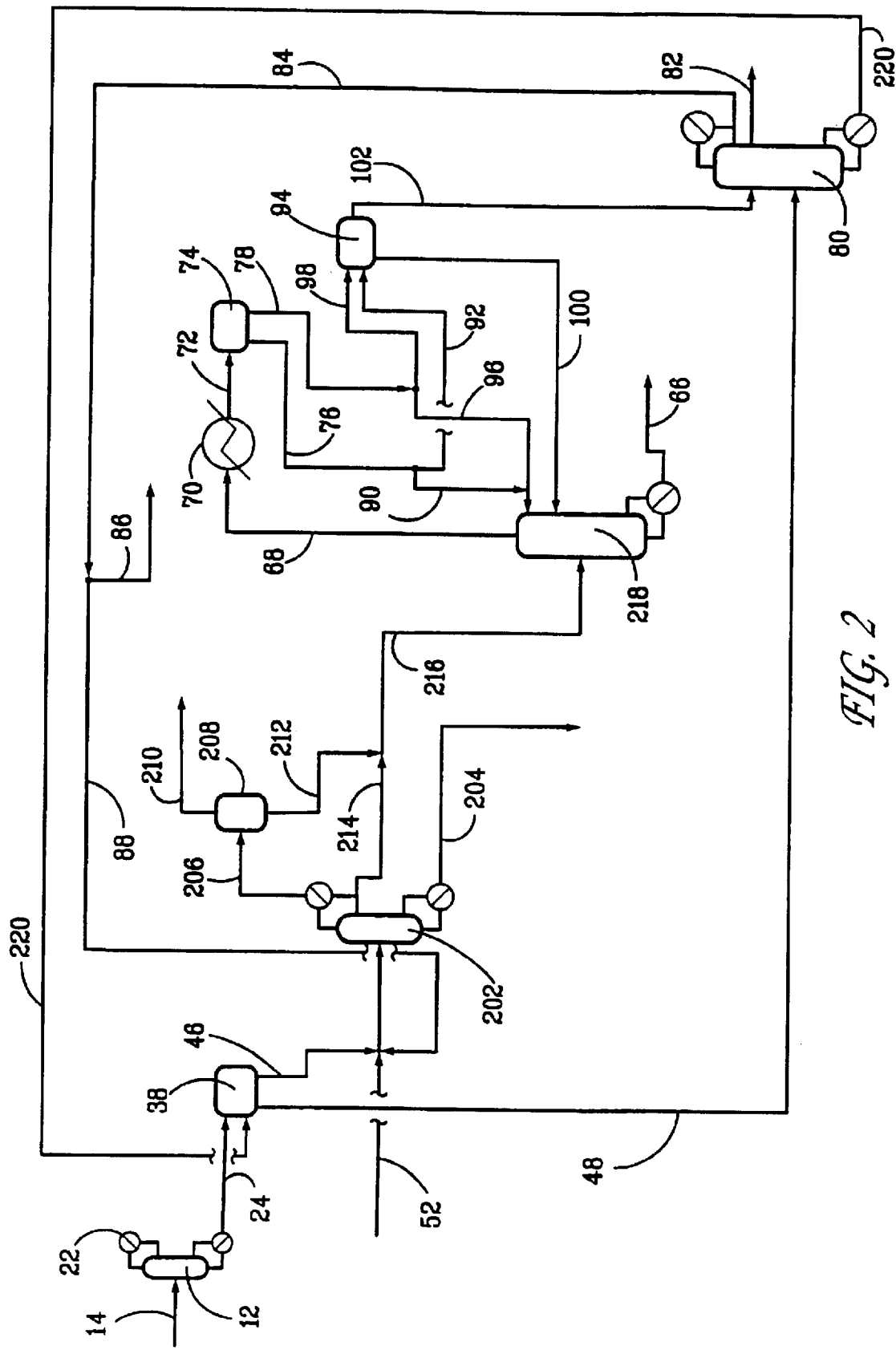
FIG. 2 represents a simplified flow diagram of a process according to a second embodiment of the invention for producing methyl isobutyl ketone.

Referring to FIG. 2, reference numeral 200 generally indicates a process according to a second embodiment of the invention, for producing methyl isobutyl ketone.

Parts of the process 200 which are the same or similar to those of the process 10 hereinbefore described with reference to FIG. 1, are indicated with the same reference numerals.

The process 200 also includes the catalytic distillation unit 12; however, the bottoms withdrawal line 24 from the catalytic distillation unit 12 leads directly to the separator or decanter 38, with the line 46 from the decanter 38 leading to a second catalytic distillation column 202. A heavy product bottoms withdrawal line 204 leads from the bottom of the column 202 while a vapour phase withdrawal line 206 leads from the top of the column 202 to a flash drum 208. An overheads flow line 210 leads from the top of the flash drum 208 while a liquid withdrawal line 212 leads from the bottom of the flash drum 204. The line 212 joins a liquid overheads withdrawal line 214 leading from the top of the column 202, to form a line 216, which leads to a distillation column 218. The bottoms withdrawal line 66 leads from the bottom of the distillation column 218, while the flow line 68 leads from the top of the column 218.

The flow line 88 leads into the flow line 52 upstream of the catalytic distillation unit 202.

A bottoms withdrawal line 220 leads from the bottom of the distillation column 80 to the separator 38.

In use, fresh acetone is fed into the catalytic distillation column 12. The column 12 is run under total reflux, and the loading of the column 12 is controlled so that the acetone undergoes an aldol condensation reaction to form MSO, DAA and reaction water, with complete or near complete acetone conversion to DAA, MSO and water. The column 12 operates under the following reaction parameters: temperature of about 120° C. in the reaction zone; temperature of about 134° C. in the reboiler; a pressure of about 6.1 bar(abs.); and total reflux. The bottoms product withdrawn from the catalytic distillation column 12 comprises, by mass, about 78% MSO, 14% water, 3% DAA, about 3% by-products, and less than 0.1% acetone.

The bottoms product stream is decanted in the decanter or separator 38. A recycle stream, passing along the flow line 220 from the water purification distillation unit 80, is mixed with the product stream from the catalytic distillation unit 12, before decanting in the decanter 38. The MSO rich product from the decanter 38 is fed, along the line 46, to the catalytic distillation unit 202, where the MSO is hydrogenated, by reaction with hydrogen entering along the flow line 52, to MIBK. The catalytic distillation column 202 is packed with a nickel based catalyst, and contains 30 theoretical reaction stages starting from the top of the column. There are 20 theoretical separation stages below the catalyst bed. The feed enters midway between the top and the bottom of the column.

Hydrogenation of the MSO to MIBK possibly results in the following reactions taking place:

Acetone→Isopropanol  (1)

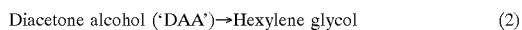
Diacetone alcohol ('DAA')→Hexylene glycol  (2)

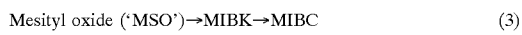
Mesityl oxide ('MSO')→MIBK→MIBC  (3)

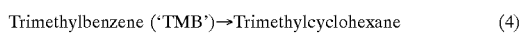
Trimethylbenzene ('TMB')→Trimethylcyclohexane  (4)

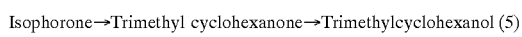
Isophorone→Trimethyl cyclohexanone→Trimethylcyclohexanol (5)

Phorone→Dimethyl-iso-butyl ketone ('DIBK')  (6)

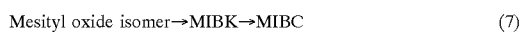
Mesityl oxide isomer→MIBK→MIBC  (7)

All heavy components, such as unreacted DAA, TMB, phorones and isophorones, hexylene glycol, trimethyl cyclohexanone and DIBK are removed as a bottoms stream along the flow line 204. Any unreacted acetone, isopropanol, MIBK, trimethylcyclohexane, MIBC and water, together with unreacted hydrogen, constitute overheads produced in the catalytic distillation unit 202.

A partial vapor liquid condenser is used in the catalytic distillation unit 202, to ensure that the overheads temperature remains high enough to use cooling water only for condensation. As a result, the overheads are partially in vapor and partially in liquid form. The vaporized overheads are withdrawn along the flow line 206 and flashed in the flash drum 208 to remove, any unreacted hydrogen which is flared along the line 210. The liquid from the flash drum is mixed with the liquid overheads withdrawn from the catalytic distillation unit 202 along the flow line 214, and passes as a combined stream along the flow line 216 to the distillation column 218.

On-spec MIBK is removed from the distillation column 218 as a bottoms stream, along the flow line 66. All heavy by-products would have been removed in the catalytic distillation unit 202; accordingly, no additional polishing of the MIBK stream is required.

The overheads from the distillation column 218, comprising an azeotropic mixture of water and MIBK, as well as lighter by-products such as isopropanol, trimethylcyclohexane and MIBC, is condensed in the condenser 70 and decanted in the separator 74. Some of the organic phase and some of the water phase is returned to the distillation column 218, along the flow lines 76, 90 and 78, 96 respectively, as reflux. The remainder of the organic phase as well as the remainder of the aqueous phase pass, along the flow lines 76, 92 and 78, 98 to the separator 94. The organic phase from the separator 94 passes, along the flow line 100, back to the distillation column 218, at the same position as the main feed point.

The water rich stream from the decanter 94 passes, along the flow line 102, into the water purification distillation column 80, together with the aqueous rich phase along the flow line 48. Pure water is withdrawn from the column 80 along the flow line 82, i.e. as a side stream. The overheads in the column 80 comprises mainly a mixture of MSO and water which is recycled back to the catalytic distillation column 202 along the line 84. The purge (about 40% by mass) along the flow line 86, is required to prevent light products (IPA and acetone) from building up. The bottoms product of the column 80 is a mixture of phorones and water, and is recycled back to the decanter 38 along the line 220, with the phorones eventually being removed through the bottoms stream 204 from the catalytic distillation unit 202.

In variations of the processes 10, 200, and in order to maximize production, all DAA can be reacted to MSO. A first alternative is to place a small bed of temperature and water resistant acidic catalyst near the reboiler of the catalytic distillation unit 12, and to allow for sufficient separation stages between the first reaction bed of the column 12 and the bed of temperature and water resistant acidic catalyst, to ensure that all the acetone is preferentially consumed in the first bed and all the DAA consumed in the second bed. Another alternative is to pass the MSO rich phase from the decanter 38 through a small fixed bed polishing reactor (not shown) containing acidic ion exchange resin, such as that available under the trademark Amberlyst. The DAA will then react to MSO in such a reactor.

Another variation, which will ensure that all the MSO is reacted to completion, is to locate a small polishing reactor (not shown) in the overheads line 206 from the catalytic distillation unit 202 in FIG. 2. The vapor stream from the catalytic distillation unit 202 will then not pass through the flash drum 208 but will be fed, together with liquid overheads from the catalytic distillation unit 202 and some additional hydrogen, to the polishing reactor. The product from the polishing reactor will then be flashed to remove unreacted hydrogen.

Figure 3:
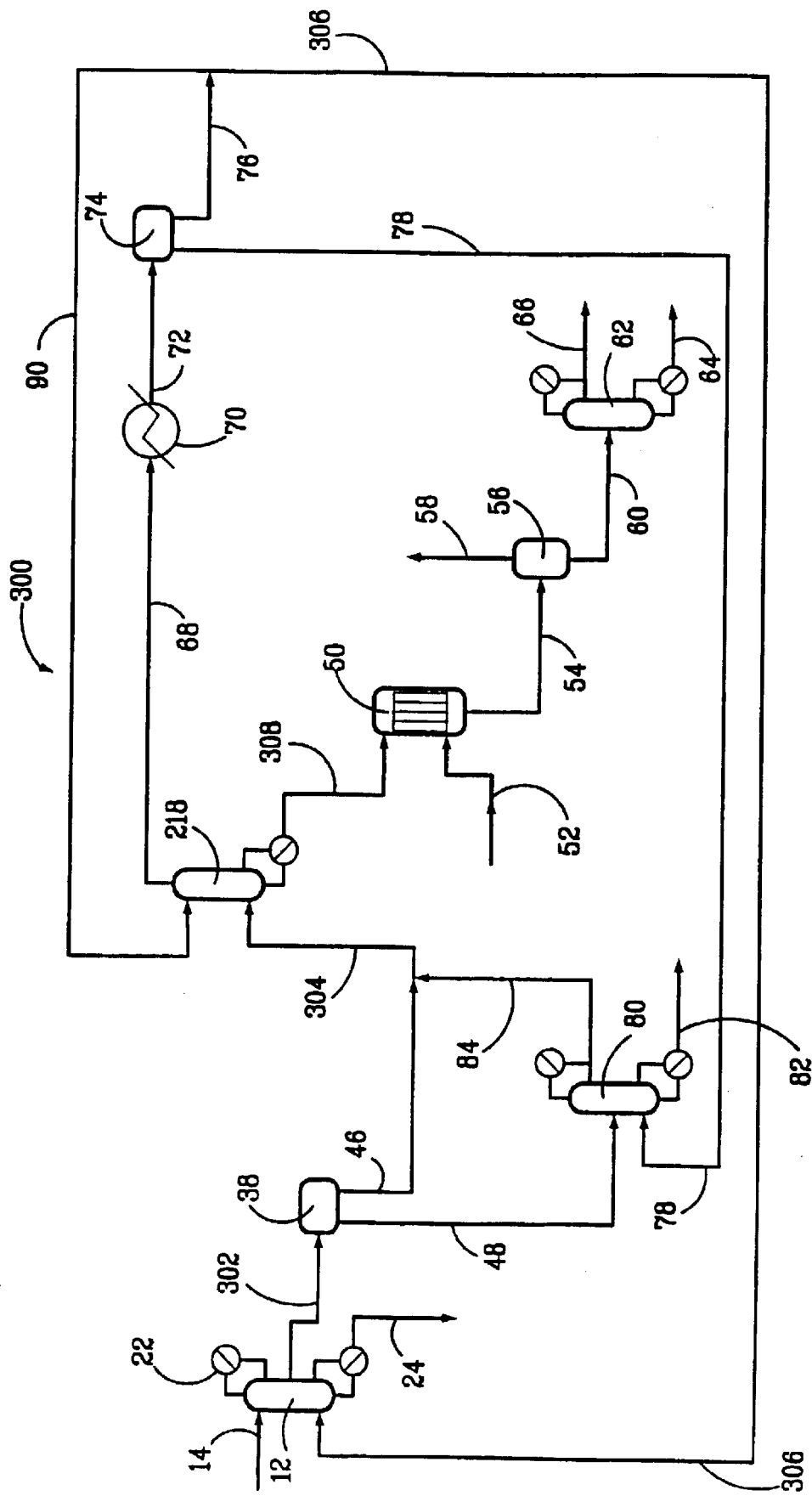
FIG. 3 represents a simplified flow diagram of a process according to a third embodiment of the invention for producing methyl isobutyl ketone.

Referring to FIG. 3, reference number 300 generally indicates a process according to a third embodiment of the invention, for producing methyl isobutyl ketone.

Parts of the process 300 which are the same or similar to those of the processes 10, 200 hereinbefore described with reference to FIGS. 1 and 2 respectively, are indicated with the same reference numerals.

The process 300 includes the catalytic distillation unit 12. The feed flow line 14 enters the unit 12 at the top of the catalyst bed. An acetone recycle line 306 leads into the catalytic distillation unit 12 just below the catalyst bed. The acetone recycle line 306 leads from the organic phase withdrawal line 76 leading from the separator 74.

The catalytic distillation unit 12 has 21 theoretical reaction stages containing Amberlyst 15 (trademark) ion exchange resin as catalyst. Typically, the catalyst can be packed into structured packing, such as that available from Catalytic Distillation Technologies of 10100 Bay Area Boulevard, Pasadena, Tex. 77507, USA. Instead, the catalyst can be packed in bales such as those described in U.S. Pat. Nos. 5,942,456 and 5,431,890, which are hence incorporated herein by reference.

A side-draw line 302 leads from the column 12, halfway between the bottom of the catalyst bed and the bottom of the column. This ensures that, in use, acetone and DAA in a side stream withdrawn along the line 302 are minimized simultaneously. The side-draw line 302 leads into the decanter 38.

The water withdrawal line 48 from the decanter 38 leads to the distillation column 80, which constitutes a water recovery unit. The water phase withdrawal line 78 from the decanter 74, also leads into the distillation column 80. The distillation column 80 is a small distillation unit, typically having a diameter smaller than 0.5 m and typically containing about 18 valve trays.

The overheads withdrawal line 84 from the distillation column 80 combines with the product withdrawal line 46 from the decanter 38, to form a feed line 304 which leads into the distillation column 218 which constitutes an acetone recovery unit.

A bottoms line 308 leads from the distillation column 218 to the hydrogenation reactor 50.

In use, the process 300 operates in similar fashion to the processes 10, 200. Thus, fresh acetone is fed into the catalytic distillation column 12 along the feed line 14. Additional acetone is recycled from the acetone recovery unit 218 along the flow line 306. The recycled acetone contains MSO and about 5 wt % water. Therefore, some separation thereof in the catalytic distillation unit 12 is required, to minimize the amount of MSO that passes through the catalyst bed, thereby to minimize formation of heavy by-products. This is the reason why the recycle line 306 enters the catalytic distillation unit 12 just below the catalyst bed. The catalytic distillation unit 12 is run under total reflux to ensure maximum acetone conversion.

A small bottoms stream (<5% of the total product streams) rich in trimethylbenzene ('TMB'), phorones, isophorones, non-decomposed DAA and MSO is removed continuously along the bottoms withdrawal line 24.

The majority of the product is withdrawn along the side-draw line 302 as a side stream. The side stream thus passes to the decanter 38 where a water-rich phase (about 92 wt % water) is removed, and sent to the water recovery unit 80. An additional water-rich stream from the decanter 74 is also fed into the water recovery unit 80. Water is removed from the water recovery unit 80 as a bottoms stream along the bottoms withdrawal line 82, while the overheads, comprising a water/MSO/acetone tertiary azeotropic mixture, is withdrawn along the line 84 and is mixed with an organic-rich phase from the decanter 38, which passes along the flow line 46, with the combined mixture then passing along the flow line 304 into the acetone recovery unit 218. The organic-rich phase from the decanter 38 contains about 90 wt % MSO.

The resultant combined or mixed feed to the acetone recovery or buffer unit 218 comprises about 5 wt % acetone, 1 wt % DAA, 89 wt % MSO and 5 wt % water. This applies to expected end-of-run conditions, and the acetone content should be less than 1 wt % at start-up. The overheads from the acetone recovery unit, which passes along the line 68, is a two-phase mixture, and thus requires the use of the condenser 70 and the decanter 74. The vapor from the recovery unit 218 is cooled in the condenser 70, and then decanted in the decanter 74, to ensure that the reflux to the acetone recovery unit 218 consists of one phase only. This reflux passes to the acetone recovery unit 218 along the line 90. A water-rich stream from the decanter 74 passes to the water recovery unit 80, as hereinbefore described. The organic phase from the decanter 74, which leaves the decanter 74 along the flow line 76, is split, with 30 wt % being returned as reflux to the acetone recovery unit 218 along the line 90, while 70 wt % is returned to the catalytic distillation unit 12 along the flow line 306, to prevent acetone build-up.

The bottoms from the acetone recovery unit 218 is rich in MSO (over 98 wt %) and passes to the hydrogenation reactor 50. The reactor 50 can be a conventional fixed bed reactor. The reactor 50 operates at 15 bar(g) and 150° C. The reactor 50 contains a 0.5 wt % palladium on alumina catalyst which is selective towards MIBK formation, and minimizes MIBC formation.

Hydrogenation of the MSO to MIBK possibly results in products being formed in accordance with reactions (1) to (7) as hereinbefore described.

It is expected, in the process 300, that reactions (1), (4), (5) and (6) will not be significant. The subsequent reaction of MIBK to MIBC is expected to be minimal due to the selective nature of the catalyst.

The product from the reactor 50 passes, along the line 54, to the flash drum 56 to remove any unreacted hydrogen. The liquid product from the flash drum 56 passes along the line 60 to the distillation column 62 which constitutes a MIBK purification unit. Any heavy components and unreacted MSO are removed along the bottoms withdrawal line 64, while on-spec (>99.5 wt %) MIBK is withdrawn as overheads, along the overhead line 66.

Expected unit conditions and configurations for the process 300 are given in Table 1.

TABLE 1

Expected unit conditions and configurations

| Condition | CD Unit 12 | Acetone Recovery Unit 218 | MIBK purification unit 62 | Water recovery unit 80 | Hydrogenation Reactor 50 |
|---|---|---|---|---|---|
| Pressure (bar abs) | 6.1 | 0.9 | 1.0 | 1.0 | 15.0 |
| Cat Bed temp (° C.) | 120 | 99 | 116 | 76 | 150 |
| Condenser temp (° C.) | 119 | — | — | — | — |
| Reboiler temp (° C.) | 240 | 124 | 160 | 100 | — |

TABLE 1-continued

Expected unit conditions and configurations

| Condition | CD Unit 12 | Acetone Recovery Unit 218 | MIBK purification unit 62 | Water recovery unit 80 | Hydrogenation Reactor 50 |
|---|---|---|---|---|---|
| Reflux ratio | Total reflux | 0.2 | 1.0 | 10.0 | — |
| Total no of separation stages | 3 above cat bed 14 below | 23 | 29 | 18 | — |
| Feed 1 | Fresh acetone Directly above cat bed | MSO Stage 10 | MIBK Stage 17 | From Decanter 38 Stage 15 | — |
| Feed 2 | Recycled acetone 2 stages below cat bed | — | — | From Decanter 74 Stage 15 | — |
| Side-draw | 8 stages below cat bed | — | — | — | — |

The process 300 will have the same advantages as the processes 10, 200. However, it is believed that the process 300 will have some additional advantages. Firstly, a unique feature of the process 300 is the removal of the product from the catalytic distillation unit 12, as a side stream located approximately halfway between the bottom of the catalyst bed and the bottom of the column. By adopting this configuration, the reboiler temperature can be raised to 240° C. or greater, depending on how much MSO is allowed to report to the bottoms. Inherently, the bottoms flow rate is also reduced, and hence the residence time of any product in the reboiler is greatly increased. By taking advantage of the propensity for DAA to decompose under high temperatures (>180° C.), DAA production is thereby minimized. The advantage of this is that the amount of DAA and hence heavy components, that report to the side-draw stream, i.e. to the product, is reduced to acceptable levels, such that a further heavies removal unit is no longer needed. In other words, all heavy components (DAA, phorones, isophorones, trimethylbenzene and others) are removed simultaneously in the catalytic distillation unit 12 by means of the bottoms stream along the line 24.

The process 300 includes the acetone recovery or buffer unit 218 which allows for the recovery of small amounts of acetone (up to 5%) which may break through to the side-draw product stream, particularly towards end-of-run conditions.

A further advantage of the process 300 is that the total number of units is kept to a minimum (4 columns and 1 reactor), and it is believed that the economics of the process 300 should thus be more favorable than with conventional processes employing more processing units.

It is known that acetone can be reacted to MIBK in a one-step process, using a fixed bed reactor containing an acidic ion exchange resin impregnated with a small fraction of about 0.5 weight % palladium. However, the catalyst lifetime is short, for example it must be regenerated every three months and replaced every nine months. Some of the acetone is converted to isopropanol which is usually incinerated, and MIBK losses are high since the separation between MIBK and MIBC which is formed, is poor. Another disadvantage is that the isopropanol cannot be removed easily, and an additional two units or stages are required for extraction and drying thereof. Thus, the number of units in the known fixed bed process is increased substantially as a result of the by-products that are formed.

In contrast, the process 10 according to the first embodiment of the invention, is one in which the loading of the catalytic distillation column 12 cannot be increased due to limitations such as flooding. In the process 10, acetone must be recovered before hydrogenation, otherwise there will be a build-up of isopropanol in the second recycle loop. The process has, however, the advantages that acetone losses are minimized and yields are higher than in the known fixed bed process. Additionally, catalyst lifetime is expected to be substantially longer, and the process is economically more viable than the known fixed bed process.

In the process 200, complete conversion of acetone is achieved in the catalytic distillation unit 12. An acetone recovery unit is accordingly not required in the downstream processing. Additionally, DAA may also be reacted to completion by using a polishing reactor as hereinbefore described. A unique feature of the process 200 is the use of the second catalytic distillation column 202. This provides the additional advantages that

- the exotherm can be controlled by controlling the column pressure and ensuring sufficient reflux; as a result, MIBC formation will be minimized
- one less unit is required
- separation of the heavy components from both the aldol condensation reaction and the hydrogenation reaction, from the product stream is performed simultaneously
- operating conditions are milder than with normal or known hydrogenation units
- catalyst lifetime should be longer since heavy by-products do not come into contact with the catalyst The process 200 has the additional advantages that only four main processing units are required to produce MIBK, i.e. excluding any small polishing reactors. MIBK losses are kept to a minimum. The process is substantially more economically viable than the known process using fixed bed reactors.

Both the processes 10, 200 thus have substantial advantages over the known fixed bed processes including improved catalyst lifetime, fewer processing units, and better return on investment.

What is claimed is:

1. A process for producing methyl isobutyl ketone, which process includes
   introducing acetone as a feedstock into a first reaction zone;
   subjecting the acetone to catalytic distillation in the first reaction zone, thereby to convert at least some of the acetone to mesityl ('MSO') and water;
   withdrawing from the first reaction zone, a product stream comprising MSO and water;
   feeding the product stream, as well as hydrogen, into a second reaction zone in which MSO present in the product stream and hydrogen react to form methyl isobutyl ketone ('MIBK'); and
   withdrawing a MIBK rich product stream from the second reaction zone.

2. A process according to claim 1, wherein an acidic catalyst is used in the catalytic distillation.

3. A process according to claim 2, wherein the catalytic distillation catalyst is a cation exchange resin.

4. A process according to claim 1, wherein the first reaction zone is provided by a column containing a packed bed of the catalyst in particulate form, with distillation media being provided in the column below, above or below and above the catalyst bed, in at least one distillation zone of the column.

5. A process according to claim 4, wherein the temperature in the catalyst bed is from 100° C. to 135° C.

6. A process according to claim 5, wherein diacetone alcohol ('DAA') MSO, water and other by-products that are formed and condensed unreacted acetone pass to the bottom of the column, where these components are reboiled in a reboiling stage located at the bottom of the column.

7. A process according to claim 6, wherein all unreacted vaporized acetone is withdrawn from the top of the column, condensed, and is returned as a reflux to the column, at or above the catalyst bed, with the catalytic distillation column thus running under total reflux.

8. A process according to claim 7, wherein the catalytic distillation column is operated such that up to about 25%–30% by mass of the acetone introduced as the feedstock, remains unreacted, with diacetone alcohol (DAA), trimethylbenzene ('TMB'), phorone, isophorone and other heavier by-products forming during the catalytic distillation, so that the product stream, which is withdrawn as a bottoms stream, comprises, in addition to the DAA, MSO, water and the by-products, also a significant proportion of unreacted acetone.

9. A process according to claim 8, wherein the catalytic distillation column is operated at a temperature of 100° C.–120° C. in the catalyst bed; a temperature of 120° C. to 150° C. in the reboiling stage; and a pressure of 2–7 bar(abs.).

10. A process according to claim 8, which includes the treatment of the product stream in at least one treatment zone, to remove a portion of the unreacted acetone, DAA, TMB, phorone, isophorone, any other heavier by-products, and water present in the product stream.

11. A process according to claim 10, which includes feeding the product stream from the catalytic distillation unit into a first treatment zone in the form of a first treatment distillation column from which a phorone rich bottoms stream, a DAA and TMB rich side stream, and the phorone- and TMB poor overheads product stream are withdrawn; and feeding the product stream from the first distillation column into a second treatment distillation column from which a MSO rich bottoms product stream and a MSO poor acetone rich overheads stream are withdrawn, with the acetone rich overheads stream from the second treatment distillation column optionally being returned to the catalytic distillation column, as a portion of the feedstock to the catalytic distillation column.

12. A process according to claim 7, wherein the catalytic distillation column is operated so that substantially all of the acetone is converted, with diacetone alcohol (DAA) forming during the catalytic distillation, so that the product stream, which is withdrawn as a bottoms stream, comprises MSO, DAA and water.

13. A process according to claim 12, wherein the catalytic distillation column is operated at a temperature of 100° C.–120° C. in the catalyst bed; a temperature of 120° C.–150° C. in the reboiling stage; and a pressure of 2 bar to 7 bar(abs.).

14. A process according to claim 7, wherein a bottoms stream comprising mainly heavy by-products, non-decomposed diacetone alcohol (DAA), and MSO, and a side stream comprising MSO and water, are withdrawn from the catalytic distillation column, with the catalytic distillation column being operated at a temperature of 100° C.–120° C. in the catalyst bed; a temperature of 120° C. to 300° C. in the reboiling stage; and a pressure of 2 bar to 7 bar(abs.).

* * * * *